United States Patent
Schuermann

(10) Patent No.: US 6,869,941 B2
(45) Date of Patent: Mar. 22, 2005

(54) COMBINATION OF DROSPIRENONE AND AN ESTROGEN SULPHAMATE FOR HRT

(75) Inventor: Rolf Schuermann, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 10/194,970

(22) Filed: Jul. 15, 2002

(65) Prior Publication Data

US 2003/0050289 A1 Mar. 13, 2003

Related U.S. Application Data

(60) Provisional application No. 60/304,760, filed on Jul. 13, 2001.

(30) Foreign Application Priority Data

Jul. 13, 2001 (DK) .................................. PA 2001 01109

(51) Int. Cl.[7] .............................................. A61K 31/56
(52) U.S. Cl. ...................................................... 514/170
(58) Field of Search ........................................ 514/170

(56) References Cited

U.S. PATENT DOCUMENTS

| | | | | | |
|---|---|---|---|---|---|
| 3,942,641 A | * | 3/1976 | Segre | ........................ | 206/534 |
| 4,129,564 A | | 12/1978 | Wiechert et al. | | |
| 5,827,843 A | | 10/1998 | Koninckx | | |
| RE36,247 E | * | 7/1999 | Plunkett et al. | ............. | 514/170 |
| 6,569,844 B1 | * | 5/2003 | Schwarz et al. | ............ | 514/176 |
| RE38,253 E | * | 9/2003 | Spona et al. | ................. | 514/170 |
| 2002/0132801 A1 | * | 9/2002 | Heil et al. | ................... | 514/175 |

FOREIGN PATENT DOCUMENTS

| | | |
|---|---|---|
| DE | 44 29 398 A1 | 2/1996 |
| WO | WO 93/05064 A1 | 3/1993 |
| WO | WO 95/07081 A1 | 3/1995 |
| WO | WO 98/06738 A1 | 2/1998 |
| WO | WO 98/24801 A1 | 6/1998 |
| WO | WO 98/27929 A2 | 7/1998 |
| WO | WO 00/06175 A1 | 2/2000 |
| WO | WO 01/12801 A2 | 2/2001 |
| WO | WO 01/52857 A1 | 7/2001 |

OTHER PUBLICATIONS

Norman et al., "Drospirenone", Drugs of the Future, 25(12), 1247–1256, 2000.*
Krattenmacher, "Drospirenone: pharmacology and pharmacokinetics of a unique progestogen", Contraception, 62, 29–38, 2000.*
English language Abstract of WO 00/06175, 2000.*
English language Abstract for WO/00/06175, 2000.
English language Abstract for WO/98/27929, 1998.
English language Abstract for DE 3022337, 1980.
Oettel, et al., "Trends and perspectives of drug development for horomone replacement in women and men," *Abstracts*, S–14, p. 254, 2000.
Norman et al., "Drospirenone," *Drugs of the Future*, 2000, 25(12): 1247–1256.
Krattenmacher, "Drospirenone: pharmacology and pharmakinetics of a unique progestogen," *Contraception*, 62 (2000), XP–000993492, pp. 29–38.
Casper et al., "Estrogen and interrupted progestin: A new concept for menopausal hormone replacement therapy," *Am. J. Obstet. Gynecol.*, vol. 168, No. 4, pp. 1188–1196, 1993.

* cited by examiner

Primary Examiner—Barbara P. Badio
(74) Attorney, Agent, or Firm—Millen, White, Zelano, Branigan, P.C.

(57) ABSTRACT

A pharmaceutical dosage unit comprising drospirenone and an estrogen sulphamate, such as an estradiol sulphamate or an estriol sulphamate for use in hormone replacement therapy is disclosed. This, combination therapy may comprise continuous or discontinuous administration of drospirenone and/or the estrogen sulphamate, such as weekly administration of both agents or weekly administration of the estrogen sulphamate and daily administration of the drospirenone.

71 Claims, No Drawings

COMBINATION OF DROSPIRENONE AND AN ESTROGEN SULPHAMATE FOR HRT

This application claims the benefit of the filing date of U.S. Provisional Application Ser. No. 60/304,760, filed Jul. 13, 2001.

FIELD OF THE INVENTION

The present invention relates to a pharmaceutical dosage unit comprising drospirenone and an estrogen sulphamate, such as an estradiol sulphamate or an estriol sulphamate, and to methods of hormone replacement therapy by administration of drospirenone and an estrogen sulphamate to estrogen-deficient women.

BACKGROUND OF THE INVENTION

Estrogen plays an important role in protecting the health of women such as protecting and maintaining cardiovascular health, bone mass, and mental cognition. However, normal ageing process results in lower levels of estrogen in women and the estrogen level may be significantly reduced upon entering menopause or upon surgical removal of the uterus and/or ovaries, for which reason those women risk the development of cardiovasculary diseases, bone mineralisation and/or poor mental cognition. Loss of bone mineral density is the key indicator of osteoporosis.

Reduced estrogen levels have also been implicated in the development of urinary incontinence as a result of the effect of the loss or estrogen on the smooth muscle cells of the urethra. Reduced estrogen levels may also be implicated in significant weight and fat mass gain in postmenopausal women.

Hormone replacement therapy has aimed to improve the quality of life of women during this natural ageing process to alleviate symptoms associated with this time of transition and to reduce the likelihood or slow the progression of disorders and diseases associated with reduced estrogen activity.

One principal aim of hormone replacement therapy is to restore levels of the sex steroid hormones in naturally or prematurely pre-menopausal, menopausal and post-menopausal women or to establish these levels in hypogonadal females.

One form of hormone replacement therapy relates to monotherapy, also referred to as unopposed therapy, wherein the woman is treated with estrogens alone. However, exogenous estrogens stimulate the proliferation of the endometrium, which may result in in the development of hyperplasia, a risk factor for endometrial cancer.

A second form of hormone replacement therapy relates to combination therapy, also referred to as opposed therapy, wherein the woman is treated with a combination of an estrogen and a progestagen. Advantageously, the progestogen protects the endometrium from hyperplasia.

However, the use of natural progesterone in combination therapy is limited by the low bioavailability of natural progesterone, even in micronized form. Significantly, it has been found that combination therapy comprising the use of drospirenone as a progestogen, is remarkably effective. Drospirenone (drospirenone), a 17-α-spirolactone derivative, is a synthetic progestagen that has a surprisingly similar physiological profile to progesterone yet notably better bioavailability. It is the first synthetic progestagen to have a progesterone-like pharmacological profile in that it has antiestrogenic, antiandrogenic and anti-mineralcorticoid activity.

The progestogenic activity of drospirenone and its consequent utility as a contraceptive agent at dosage levels of 0.5–50 mg is disclosed in DE 30 22 337. The anti-mineralcorticoid activity of drospirenone limits the increase in weight gain that is observed in women taking estrogens by reduction of the estrogen-induced sodium and water retention. The anti-mineralcorticoid effect is also known to have beneficial and preventive effects on hypertension. The anti-androgenic activity of drospirenone may suppress unwanted symptoms such as acne and changes in hair pattern, hair distribution, and hair growth such as in hirsutism, by inhibiting androgenic receptors in the skin. The pharmacological activities of drospirenone is described in Krattenmacher, Rolf, *Contraception* (62) 2000, pp 29–38; *Drospirenone: pharmacology and pharmacokinetics of a unique progesterone*. The activity of drospirenone is further described in *Drugs of the Future* 2000, 25(12), pp 1247–1256.

Drospirenone is also known from DE 26 52 761 in which its use as a diuretic is disclosed.

The use and role of progestogens in opposed forms of hormone replacement therapy has been studied by the scientific community (Lobo R. A., 1992; Sobel N. B., 1994) as have been regimens comprising estrogens and progestogens (Corson S. L., 1993, ones K. P., 1992).

Various regimens for hormone substitution have been disclosed. For example the use of a preparation for hormone substitution therapy comprising at least one progestagen and at least one estrogen wherein the estrogen dose varies with a periodicity such that blood loss is substantially avoided is disclosed in WO 95/07081. Furthermore, a regimen involving interrupted administration of progestin in the presence of continuous estrogen is disclosed (Casper R. F. et al., Am J Obstet. Gynecol. vol 168, no 4, p 1188–1983).

The use of a therapeutic gestagen such as drospirenone, possibly in combination with an estrogen for the treatment of Premenstrual Dysphoric Disorders (PMDD) is disclosed in WO 98/27929.

Also various pharmaceutical compositions comprising drospirenone have been reported, for example, a pharmaceutical composition comprising a combination of ethinyl estradiol and drospirenone for use as a contraceptive is disclosed in WO 01/12801.

Estrogen sulphamates, such as estradiol sulphamate, may be viewed as prodrugs, which, upon enzymatic hydrolysis by sulphatases in vivo, are split into the estrogen, such as estradiol, and a sulphamic acid. The use of estrogen sulphamates for oral discontinuous application for hormone replacement therapy is disclosed in WO 00/06175. The discontinuous method of administration is such that the administration can take place at intervals ranging from 2 to 40 days. WO 00/06175 also relates to the additional administration of gestagens, preferably continuously in the form of an implant or in the form of an intrauterine releasing system.

Estradiol sulphamates were first disclosed in WO 93/05064 in connection with the findings that estrone sulphamates showed excellent sulphatase inhibiting activity for which reason it may be used in the treatment of estrone dependent rumors, especially breast cancer.

The invention relates to the use of a combination of drospirenone and an estradiol sulphamate in hormone replacement therapy.

SUMMARY OF THE INVENTION

The present investigators have found that the particular combination of an estrogen sulphamate and drospirenone is remarkably effective for use in hormone replacement therapy.

Thus, in a first aspect, the invention relates to a pharmaceutical composition in the form of a dosage unit comprising a combination of an estrogen sulphamate and drospirenone together with one or more pharmaceutically acceptable carriers or excipients. In a presently preferred embodiment, the estrogen sulphamate is the unsubstituted 17-estradiol-sulphamate.

A second aspect of the present invention relates to the use of a combination of drospirenone and an estrogen sulphamate for the preparation of a medicament comprising a sufficient dose of the estrogen sulphamate for the treatment of diseases, disorders or symptoms associated with deficient endogenous levels of estrogen in a woman.

Correspondingly, a method of treating diseases, disorders and symptoms associated with deficient endogenous levels of estrogen in a woman comprising administering a sufficient dose of estrogen sulphamate to alleviate said diseases, disorders and symptoms in combination with drospirenone. Thus, the method comprises the administering of an estrogen sulphamate in sufficient amounts to alleviate said diseases, disorders and symptoms and drospirenone.

A still further aspect of the invention relates to a pharmaceutical kit comprising up to 70 dosage units or multiples thereof, wherein at least 3 said dosage units within one multiple of units comprise an estrogen sulphamate and at least 3 said dosage units within one multiple of units comprise drospirenone and wherein optionally up to 64 of said dosage units within one multiple of units comprise a placebo or a blank.

DETAILED DESCRIPTION OF THE INVENTION

The term "an estrogen sulphamate" is intended to mean one or more sulphamate esters of an estra-1,3,5(10) triene and pharmaceutically acceptable salts thereof, wherein the triene has at least one hydroxy group. More specific, an estra-1,3,5(10) triene may contain one, two or three free hydroxyl groups. In suitable embodiments of the invention, such trienes is an estrone, an estradiol or an estriol, preferably an estradiol or an estriol. The term "sulphamate ester" is intended to mean an ester with sulphamic acid or with N-substituted sulphamic acid, wherein the N-substituted sulphamic acid may be an N-alkyl, N-cycloalkyl, N-alkenyl or an optionally substituted N-aryl. The N-alkyl, N-cycloalkyl and N-alkenyl may consist of up to 7 carbon atoms, but 1, 2, 3, or 4 carbon atoms are preferred. The optionally substituted N-aryl relates to where one or more hydrogen atoms are replaced by an alkyl, a cycloalkyl or an alkenyl. The alkyl, cycloalkyl and alkenyl may consist of up to 7 carbon atoms, but 1, 2, 3, or 4 carbon atoms are preferred. In general, the N-substituted sulphamic acid may be selected from the group comprising N-alkyl, N-cycloalkyl, N-alkenyl and N-aryl derivatives of sulphamic acid as described in patent WO 93/05064.

Moreover, the term "an estrogen sulphamate" relates also to sulphamate esters of conjugated estrogens.

In specific embodiments of the invention, the estrogen sulphamate is a 17-estradiol, a derivative or a pharmaceutically acceptable salt thereof esterified with sulphamic acid or a N-substituted sulphamic acid. In other embodiments of the invention, the estrogen sulphamate is an estriol or an estrone their derivatives or pharmaceutically acceptable salts esterified with sulphamic acid or with N-substituted sulphamic acid.

In preferred embodiments the esterification is at the C-3 hydroxyl of said estra-1,3,5(10) triene such as at the C-3 hydroxyl group of estrone, estradiol or estriol.

Preferred estrogen sulphamates are selected from the group comprising of the unsubstituted 17-estradiol-sulphamate, unsubstituted 16,17-estriol-sulphamate, 17-estradiol-3-N,N-dimethyl sulphamate and 16,17-estriol-3-N,N-dimethyl sulphamate, most preferably the unsubstituted 17-estradiol-sulphamate.

Moreover, in some embodiments two or more different estrogen sulphamates may be used.

The term "administration" relates to the application or consumption of a dosage unit. The term "delivery" relates to the in vivo absorption of a therapeutically active amount of an agent.

The term "continuous" is intended to relate to the delivery of an agent at an interval period, wherein delivery of the agent is maintained for the duration of the interval period. For example, the administration every day of the agent in a dosage effective throughout the daily interval, the administration every third day of the agent in a dosage effective throughout the 3 day interval, the administration every week of a dosage effective throughout the 7 day interval, or the administration every month of a dosage effective throughout the one month interval. Furthermore, continuous delivery may involve administration of an agent for three days followed by three days of no administration such as 3-days-on-3-days-off administration, which in the case of continuous delivery may result in at least 6 days delivery of an agent. Likewise, continuous delivery of an agent upon administration in a 7-days-on-7-days-off manner may result in at least 14 days delivery of an agent.

The term "discontinuous" involves the interrupted delivery of an agent, wherein the period of interruption is not equivalent to the period of delivery or to the duration of the effect of an agent. The administration of an agent every third day delivering an effective dosage throughout only 1 day or 2 days are typical discontinuous regimens of 1-day-on-2-days-off and 2-days-on-1-day-off, respectively. Discontinuous delivery involving administration of an agent once a week as a 1-day-on-6-days-off, 3-days-on-4-days-off, 2-days-on-5-days-off are typical discontinuous delivery regimens. Another discontinuous delivery involves delivery of an agent for 21 days follow by a period of interruption for 7 days as a 21-days-on-7-days-off cycle. Typical examples of such a cycle include administration or delivery of an agent for 21 days followed by 7 days of no administration or delivery of an agent; and weekly administration of an agent for delivery of agent throughout the week for 3 weeks followed by one week of no administration of agent.

Furthermore, discontinuous delivery may involve administration of an agent for three days followed by three days or no administration such as 3-days-on-3-days-off administration, which in the case of discontinuous delivery may result in 3 to 5 days delivery of an agent. Likewise, discontinuous delivery of an agent upon administration in a 7-days-on-7-days-off manner may result in 7 to 13 days delivery of an agent. The period of interruption relates to the period, wherein an agent is not delivered.

A sequential administration may result in discontinuous or continuous delivery of an agent. An example of a sequential administration resulting in a continuous delivery is the weekly administration of an agent effective for the duration of the week. An example of a sequential administration resulting in a discontinuous delivery is a monthly administration of an agent effective for only 21 days.

The term "interval" in connection with the treatment is intended to relate to the period of time between administration of an agent such as the number of days between taking an oral formulation, applying a new transdermal patch, (self)-administering an injection. Each administration is that of a dosage unit.

Accordingly, in the embodiment that an oral formulation comprising an estrogen sulphamate and drospirenone is administered every week and delivers the sulphamate for a 7-day period and drospirenone for a 3-day period, the estrogen sulphamate is delivered in a continuous manner and drospirenone is delivered in a discontinuous manner. The administration of the dosage unit is said to be on a weekly interval. Similarly, a monthly-administered transdermal patch that delivers the estrogen sulphamate for a month and drospirenone for 3 weeks delivers the estrogen sulphamate in a continuous manner and drospirenone in a discontinuous manner.

In the present context, the term cycle itself or when associated with the term menstrual is intended to mean the number of days between menses in a woman. It can range from 21–35 days, typically 28 days.

In the present context, the term menopause is understood as the last natural (ovary-induced) menstruation. It is a single event and a result of an age-dependent dysfunction of the ovarian follicles. Menopause results from the ovaries decreasing their production of the sex hormones estrogen and progesterone. When the number of follicles falls below a certain threshold (a bleeding threshold), the ovaries can no longer produce mature follicles and sex hormones. The ability to reproduce ends with menopause.

The peri-menopausal phase begins with the onset of climacteric symptoms when the cycle becomes irregular and ends one year after menopause. The end of peri-menopausal phase can be identified after a protracted period of time without bleeding. Post-menopause is the phase that begins at menopause and continues until death.

As stated, a first aspect of the invention relates to a pharmaceutical dosage unit in the form of a dosage unit comprising a combination of an estrogen sulphamate and drospirenone together with one or more pharmaceutically acceptable carriers or excipients.

In a particularly preferred embodiment of the invention, the dosage unit is administered weekly, such as a combined continuous administration. In a particularly preferred embodiment of the present invention, a dosage unit comprising estrogen sulphamate and drospirenone is administered weekly.

An alternative suitable embodiment, an estrogen sulphamate is administered weekly whereas drospirenone is administered daily. In a further suitable embodiment, both the estrogen sulphamate and drospirenone are administered daily.

According to the invention, the dosage unit may comprise estrogen sulphamate in a dose sufficient for the treatment of diseases, disorders or symptoms associated with deficient endogenous levels of estrogen in a woman. Typically, the deficient endogenous levels of estrogen are caused by natural menopause, pre-menopause, peri-menopause, post-menopause, hypogonadism, castration, hysterectomy, or primary ovarian failure.

As mentioned the dosage unit comprises drospirenone. The dose of drospirenone may be in a dose sufficient to exhibit its anti-androgenic and/or anti-mineralcorticoid activity in that it should be understood that the anti-androgenic and/or anti-mineralcorticoid activity relates to prevention or counteraction of the adverse effects of the estrogen sulphamate, such as adverse effects to the endometrium, prevention or lessening of weight gain; prevention or lessening of changes in hair pattern, texture, growth or distribution, such as in hirsutism.

In a suitable embodiment of the invention, the dose of an estrogen sulphamate present in a dosage unit intended for daily delivery of about 0.01 to 1 mg of the unsubstituted 17-estradiol-sulphamate, preferably of about 0.02 to 1 mg or 0.04 to 0.8 mg, more preferably of about 0.06 to 0.6 mg, most preferably of about 0.06 to 0.4 mg of the unsubstituted 17-estradiol-sulphamate.

The dose of drospirenone present in a dosage unit of a dosage unit intended for daily administration is suitably about 0.1 mg–5 mg, preferably 0.25 to 4 mg, more preferably 0.5 to 3 mg, particularly preferably 0.5 to 2.5 mg, even more preferably about 0.5 to 1.5 mg, most preferably about 0.5 to 1 mg.

Accordingly, the dose of an estrogen sulphamate in a dosage unit intended for a three-day delivery corresponds to about 0.03 to 3 mg of the unsubstituted 17-estradiol-sulphamate, preferably of about 0.06 to 3 mg or of about 0.1 to 2.5 mg, more preferably of about 0.2 to 1.5 mg, most preferably of about 0.2 to 1 mg of the unsubstituted 17-estradiol-sulphamate.

The dose of drospirenone in a dosage unit intended for a three-day delivery is typically about 0.25 mg to 15 mg, preferably 0.75 mg to 10 mg, particularly about 1 to 5 mg, such as 1, 2, 3, 4, or 5 mg most preferably about 2 to 3 mg.

In a particularly interesting embodiment of the present invention, the dosage unit is administered weekly. In such an embodiment, the dose of estrogen sulphamate in a dosage unit intended for a weekly administration typically corresponds to about 0.1 to 6 mg of the unsubstituted 17-estradiol-sulphamate, preferably of about 0.25 to 6 mg or about 0.25 to 4 mg, more preferably of about 0.25 to 3 mg, most preferably of about 0.25 to 2.5 mg or about 0.25 mg to 2 mg of the unsubstituted 17-estradiol-sulphamate. The dosage unit intended for weekly administration typically comprises drospirenone in a dose of about 1 mg to 20 mg, preferably 2 mg to 10 mg, more preferably about 2 to 8 mg, most preferably about 3 to 6 mg, such as 3, 4, 5, or 6 mg, most particularly about 4 mg.

The suitable dose of estrogen sulphamate in a dosage unit intended for administration corresponding to a full-cycle administration corresponds to a delivery of about 0.4 to 25 mg of the unsubstituted 17-estradiol-sulphamate per cycle, preferably of about 0.8 to 16 mg, more preferably of about 0.8 to 12 mg, most preferably of about 0.8 to 10 mg of the unsubstituted 17-estradiol-sulphamate.

The dose of drospirenone in a dosage unit intended for delivery corresponding to a menstrual cycle is suitably about 2 to 76 mg per cycle, preferably about 5 mg to 50 mg of drospirenone, more preferably about 8 to 30 mg, even more preferably about 10 to 25 mg, most preferably 12 to 20 mg per cycle.

In an interesting embodiment of the dosage unit of the present invention, drospirenone is formulated for slow release, a modified-release of the agent. Similarly, the estrogen sulphamate may also be formulated for slow release.

However, as is known to the person skilled in the art, an estrogen sulphamate has a sustained effect in vivo, attributed at least in part to the slow hydrolysis of the sulphamate ester to generate estradiol. This is one advantage of the use of an estrogen sulphamate over other estrogens. An estradiol sulphamate is carried by erythrocytes and avoid hepatic metabolism. Thus, lower doses may be required. Moreover, as demonstrated by the present investigator, an estrogen sulphamate inhibits sulphatases in vivo thus slowing the hydrolysis of the sulphamate ester, thus resulting in a slow release of estrogen from the estrogen sulphamate, resulting in a prolonged effect of the estrogen sulphamate in vivo.

An important object of the invention relates to the prolonged effect of drospirenone and an estrogen sulphamate upon administering the said agents from a suitable formulated dosage unit. The dosage unit of the present invention may be formulated such that a dosage unit is formulated for delivery of drospirenone in a sufficient dose to counteract or protect from the adverse effects of an estrogen sulphamate such as the adverse effects to the endometrium or in a dose sufficient for exhibiting its anti-androgenic and/or anti-mineralcorticoid activities for a period of 1 day. 3 days, 7 days, 14 days, 28 days or 1-month after administration of one of said dosage unit.

Thus, apart from other the advantages of low required doses of the estrogen sulphamate and prolonged effect of the estrogen sulphamate, such as for a week, a further advantage of the present invention is that the upper limit of the low doses of an estrogen sulphamate need not be limited for fear of resulting in hyperplasia of the endometrium. Drospirenone may be present in an amount sufficient to counter the possible adverse effects of the estrogen sulphamate or in therapeutically sufficient anti-mineralcorticoid and/or anti-androgenic amounts. Similarly, the dosage unit of the present invention may be formulated such that the dosage unit of the estrogen sulphamate is delivered in vivo in sufficient a dose to treat diseases, disorders or symptoms associated with deficient endogenous levels of estrogen in a woman throughout a period selected from 1 day, 3 days, 7 days, 14 days, 28 days or 1 month after administration of one of said dosage unit.

Hence, in suitable embodiments of the invention, the dosage unit of the invention may be formulated such that the dose of the estrogen sulphamate and the drospirenone is delivered throughout a period of 1 day, 3 days, 7 days, 14 days, 28 days or 1 month after administration of one of said dosage unit.

The dosage unit may be formulated for oral, topical, transdermal, subcutaneous or parenteral administration in a preferred embodiment, the dosage unit is formulated for oral, transdermal, transvaginal or subcutaneous administration. Moreover, in a presently preferred embodiment, the dosage unit is formulated for oral administration. Typically, the oral formulation is in the form of tablets, capsules, granules or powders, and the transdermal formulation is implantation tablets, oils or implants.

The dose of an estrogen sulphamate may vary from woman to woman, depending on the phase of her life (pre-, peri- or post-menopausal), endogenous levels of estrogen, the severity of the symptom(s), disorder or disease, the particular disorder, disease or symptom targeted, the use by the woman of other medicaments for other purposes, and other pharmacokinetic variables.

The dose of an estrogen sulphamate may also be selected so as to obtain beneficial effects on cognitive functions, depression and CNS disorders such as degenerative CNS disorders in the peri- and post-menopausal woman.

Typical diseases, disorders and symptoms associated with deficient levels of endogenous levels of estrogen are hot flushes, sweating attacks, palpitations, sleep disorders, mood changes, nervousness, anxiety, poor memory, loss of confidence, loss of libido, poor concentration, diminished energy, diminished drive, irritability, urogenital atrophy, atrophy of the breasts, cardiovascular disease, changes in hair distribution, thickness of hair, changes in skin condition, breast cancer, bone demineralisation and osteoporosis. The prevention or management of osteoporosis and bone demineralisation is a particularly interesting application of the dosage unit of the present invention.

Other than osteoporosis, further particularly interesting indications for use of the dosage unit are the for the alleviating of sleep disorders, mood changes, nervousness, anxiety, urogenital atrophy, atrophy of the breasts and for the prevention of breast cancer. The prevention of breast cancer by the dosage unit of the invention is thought to be associated with the interference of estrogen sulphamated with sulphatasea. Thus, the invention relates to a dosage unit, wherein the estrogen sulphamate is present in an amount sufficient for the treatment of breast cancer in a woman, such as estrogen-dependent breast cancer.

Deficient levels of estrogen can occur for a variety of reasons. The dosage unit can be such that it is adequate for deficient levels of estrogen, regardless of the cause. Causes anticipated by the therapy are, but not limited to, natural menopause, pre-menopause, peri-menopause, post-menopause, hypogonadism, castration or primary ovarian failure.

Low endogenous levels of estrogen, irrespective of the cause, lead to an overall decreased quality of life for women. Symptoms, diseases and disorders range from merely being inconvenient to life threatening the dosage unit of this therapy anticipates the effective alleviation of all physiological signs of estrogen deficiency.

Transient symptoms, such as vasomotor signs and psychological symptoms are certainly embodied with the realm of therapy Vasomotor signs comprise but are not limited to hot flushes, sweating attacks such as night sweats, and palpitations. Psychological symptoms of estrogen deficiency comprise, but are not limited to, insomnia and other sleep disorders, poor memory, loss of confidence, mood changes, anxiety, loss of libido, difficulties in concentration, difficulty in making decisions, diminished energy and drive, irritability, and crying spells.

The treatment of the aforementioned symptoms can be associated with the peri-menopausal phase of a woman's life or after, sometimes long after menopause. It is anticipated that the invention is applicable to these and other transient symptoms during the peri-menopausal phase, menopause, or post-menopausal phase. Moreover, the aforementioned symptoms can be alleviated if the cause of the estrogen deficiency is hypogonadism, castration or primary ovarian failure.

In another embodiment of the invention, the therapy is used for the treatment of permanent effects of estrogen deficiency. Permanent effects comprise physical changes such as urogenital atrophy, atrophy of the breasts, cardiovascular disease, changes in hair distribution, thickness of hair, changes in skin condition and osteoporosis.

Urogenital atrophy, conditions associated with it such as vaginal dryness, increase in vaginal pH and subsequent changes in flora, or events which lead to such atrophy, such as decreases in vascularity, fragmentation of elastic fibres, fusion of collagen fibres, or decreases in cell volume are symptoms thought to be particularly relevant to this therapy. Furthermore, the invention is thought to be relevant to other urogenital changes associated estrogen deficiency such as decreases in the length and/or diameter of the vagina, decreases mucus production, changes in cell population, decreases in glycogen production, decreases in growth of lactobacilli or increases in growth of *streptococci, staphylococci*, or *coliform bacilli*. Other associated changes that are thought to be preventable by the invention are those that may render the vagina susceptible to injury or infection, such as exudative discharges, vaginitis, and dyspareunia. Furthermore, infections of the urinary tract and incontinence are other common symptoms associated with lowered estrogen levels.

Other embodiments of the invention include the prevention or alleviation of physical changes associated with estrogen deficiency, such as changes in the skin, changes in hair distribution, thickness of hair, atrophy of the breasts, or osteoporosis.

The invention includes prevention of negative effects on the cognitive function and other central nervous parameters related to estrogen deficiency.

The prevention and management of osteoporosis, most notably post-menopausal osteoporosis, is a particularly interesting embodiment of the invention. Furthermore, bone demineralisation, reduction of bone mass and density, thinning and interruption of trabeculae, and/or consequent increase in bone fractures or bone deformations are thought to be particularly relevant. The prophylactic treatment of osteoporosis is an interesting therapeutic application of the invention.

The amount of drospirenone (drospirenone) in a dosage unit may depend on the dose of an estrogen sulphamate. For instance, at high doses of estrogen sulphamate, the dose of DRPS may be such that to be sufficient to protect the endometrium from the adverse effects of the levels of the estrogen and an estrogen sulphamate in the woman. Drospirenone, in sufficient doses, may be used as an opponent to estrogen to protect the endometrium from hyperplasia and/or cancer. Drospirenone may also be present in the dosage unit in relation to its combined therapeutic anti-mineralcorticoid and/or -androgenic properties and/or anti-ovulatory activities. According to said activities, drospirenone may balance the potential weight gain and potential hypertension that may follow the intake of estrogens in women. Also the activities of drospirenone on suppression of unwanted symptoms such as acne and hirsutism may be beneficial for peri-menopausal or post-menopausal women. Accordingly, the invention relates to a dosage unit, wherein drospirenone is in an amount sufficient to exhibit its anti-androgenic and/or anti-mineralocorticoid activity.

The anti-androgenic and/or anti-mineralcorticoid activity may be selected from the group consisting of prevention or counteraction of the adverse effects of an estrogen sulphamate, such as adverse effects to the endometrium; prevention or lessening of weight gain; prevention or lessening of changes in hair pattern, texture, growth, distribution, such as in hirsutism.

Drospirenone may be administered in the form of an ester or prodrug such as administered as an oxyiminopregnane carbolactone as disclosed in WO 98/24801 This prodrug to drospirenone is converted in vivo to drospirenone.

Given drospirenone is not particularly amenable to transdermal delivery, in one embodiment of the invention, drospirenone is administered as an oxyiminopregnane carbolactone transdermally. In such an embodiment, an estrogen sulphamate may, for instance, be administered transdermally or orally.

The suitable dose according to the invention may depend on the dose required of an estrogen sulphamate, such as at low doses of an estrogen sulphamate, the adverse effects of the estrogen sulphamate are minimised, thus the amount of drospirenone may be reduced, but still be in an amount sufficient to provide any anti-androgenic and/or anti-mineralocorticoid activity in vivo.

The dosage unit formulated for oral administration may be a solid, semisolid or fluid formulation The solid dosage units may be selected from the group consisting of uncoated tablets, modified-release tablets, gastro-resistant tablets, orodispersible tablets, effervescent tablets, chewable tablets, soft capsules, hard capsules, modified-release capsules, gastro-resistant capsules, uncoated granules, effervescent granules, coated granules, gastro-resistant granules, modified-release granules, and powders for oral administration; and the fluids are selected from the group consisting of solutions, suspensions and emulsions. The dosage units for topical administration may be selected from the group consisting of creams, gels, emulsions, suspensions, lotions, suppositories, enemas, pessaries, vaginal capsules, vaginal tablets, pads, sponges, plasters and transdermal delivery systems. The dosage units for parenteral administration may be selected from the group consisting of solutions, suspensions, emulsions, gels, implantation tablets and implants.

The use of a combination of the estrogen sulphamate and drospirenone may be such that the active agents are administered concomitantly or independently. That is to say that the combination is administered in a single dosage form or as more than one dosage form such as one agent administered as a solid and the other agent as a fluid. Similarly, one agent may be formulated for oral administration whilst the other is formulated for transdermal or subcutaneous administration in a preferred embodiment, both agents are administered as solids formulated for oral administration.

The combination of an estrogen sulphamate and/or drospirenone may be administered in oral, topical, transdermal, subcutaneous, transvaginal or parenteral formulation, or mixtures thereof. The estrogen and/or drospirenone may be administered as an oral formulation, such as a tablet, from a patch, from an implant or combinations thereof. In a preferred embodiment, an estrogen sulphamate and/or drospirenone are administered in oral formulation or transdermal formulation, preferably oral formulation in a suitable embodiment, estrogen is administered as an oral formulation and drospirenone is administered as oral or transdermal formulation, preferably an oral formulation.

Moreover, an interesting embodiment of the invention comprises a dosage unit wherein the drospirenone (drospirenone) is in micronized form, such that one or both estrogen and drospirenone are in micronized form, preferably both estrogen and drospirenone are in micronized form.

Drospirenone, which may be prepared substantially as described in U.S. Pat. No. 4,129,564 or WO 98/06738, is a sparingly soluble substance in water and aqueous buffers at various pH values. Furthermore, drospirenone is rearranged to an inactive isomer under acid conditions and hydrolysed under alkaline conditions. To ensure good bioavailability of the compound, it is therefore advantageously provided in a form that promotes rapid dissolution thereof.

It has been found that when drospirenone is provided in micronized form in a pharmaceutical dosage unit, rapid dissolution of the active compound from the dosage unit occurs in vitro. A micronized substance is such that a test batch (ca. 200 mg) of the particles, herein drospirenone particles, has a surface area of more than 10,000 $cm^2/g$, and has the following particle size distribution for drospirenone as determined under the microscope: not more than 2 particles in a given batch (ca. 200 mg) with a diameter of more than 30 $\mu$m, and preferably $\leq$20 particles with a diameter of $\geq 10$ μm and $\leq 30$ μm. The term "rapid dissolution" is defined as the dissolution of at least 70% over about 30 minutes, in particular at least 80% over about 20 minutes, of drospirenone from a tablet preparation containing 3 mg of drospirenone in 900 ml of water at 37° C. determined by the USP XXIII Paddle Method using a USP dissolution test apparatus 2 at 50 rpm.

As an alternative to providing the drospirenone in micronized form, it is possible to dissolve it in a suitable solvent, e.g. methanol or ethyl acetate, and spray it onto the surface of inert carrier particles followed by incorporation of the particles containing drospirenone on their surface in the dosage unit. Another suitable administration of drospirenone is in the form of a cyclodextrin complex.

The dosage unit of the present invention comprises carriers or excipients, which may act to promote dissolution of both active substances. Examples of such carriers and excipients include substances that are readily soluble in water such as cellulose derivatives, carboxymethyl cellulose, hydroxypropyl cellulose, hydroxypropyl methyl cellulose, gelled starch, gelatin or polyvinylpyrrolidone. In particular, it is anticipated that polyvinylpyrrolidone might be particularly helpful to promote dissolution.

The term "pharmaceutically acceptable carriers and excipients" is intended to mean substances, which are substantially harmless to the individual to which the dosage unit will be administered. Such an excipient normally fulfils the requirements given by the national drug agencies. Official pharmacopeias such as the British Pharmacopeia, the United States of America Pharmacopeia and the European Pharmacopeia set standards for well-known pharmaceutically acceptable excipients.

Suitable pharmaceutically acceptable excipients according to the invention include all kinds that may be used for solid, semi-solid and fluid dosage units.

The excipients may include solvents, buffering agents, preservatives, humectants, chelating agents, antioxidants, stabilizers, emulsifying agents, suspending agents, gel-forming agents, diluents, disintegrating agents, binding agents, lubricants, coating agents and wetting agents. Typically, the diluents and disintegrating agents may be lactose, saccharose, amdex, calcium phosphates, calcium carbonate, calcium sulphate, mannitol, starches and microcrystaline cellulose.

Binding agents are but not limited to saccharose, sorbitol, gum acacia, sodium alginate, gelatine, starches, cellulose, sodium coboxymethylcellulose, methylcellulose, hydroxypropylcellulose, polyvinylpyrrolidone and polyetyleneglycol.

Typically wetting agents may be sodium laurylsulphate and polysorbate 80, and lubricants may be talcum, magnesium stearate, calcium stearate, silicium oxide, precirol and polyethylenglycol.

Coating agents are but not limited to hydroxypropylcellulose, hydroxypropylmethylcellulose, polyvinylpropylidone, ethylcellulose and polymethylacrylates.

The dosage unit may also be administered transdermally, e.g where the dosage unit is formulated as a pad, dressing, bandage, plaster or transdermal delivery systems. Suitable pharmaceutically acceptable carriers and excipients includes microspheres and liposomes.

As stated, a second aspect of the invention relates to the use of a combination of drospirenone and an estrogen sulphamate for the preparation of a medicament comprising a sufficient dose of the estrogen sulphamate for the treatment of diseases, disorders or symptoms associated with deficient endogenous levels of estrogen in a woman. Preferably, the medicament comprises drospirenone in a sufficient dose to counteract or protect from the adverse effects of an estrogen sulphamate such as adverse effects to the endometrium, or in an amount sufficient for exhibiting its anti-androgenic and/or anti-mineralcorticoid activities. Correspondingly, a method of treating diseases, disorders and symptoms associated with deficient endogenous levels of estrogen in a woman comprising administering an sufficient dose of estrogen sulphamate to alleviate said diseases, disorders and symptoms in combination with drospirenone is anticipated. Thus, the method comprises the administering of an estrogen sulphamate in sufficient amounts to alleviate said diseases, disorders and symptoms and drospirenone.

According to the invention, drospirenone and/or the estrogen sulphamate may be delivered in a continuous or discontinuous manner. In a suitable embodiment of the present invention, drospirenone is administered in a continuous manner comprising intervals of administration 1 to 30 days, preferably 1, 3, 7, 14, 28 or 30 days, most preferably 1, 7, 28, or 30 days. In a presently preferred embodiment, drospirenone is administered every 1 day.

In a further suitable embodiment of the present invention, drospirenone is delivered in a discontinuous manner such as delivery for 1 day followed by an interruption for 1 to 30 days; delivery for 2 days followed by an interruption for 1 to 29 days, delivery for 3 days followed by an interruption for 1 to 28 days, delivery for 4 days followed by an interruption for 1 to 27 days, delivery for 5 days followed by an interruption for 1 to 26 days, delivery for 6 days followed by an interruption for 1 to 25 days; delivery for 7 days followed by an interruption for 1 to 24 days; delivery for 10 days followed by an interruption for 1 to 21 days; delivery for 14 days followed by an interruption for 1 to 17 days: delivery for 17 days followed by an interruption for 1 to 14 days; delivery for 21 days followed by an interruption for 7 to 10 days; or combinations thereof.

In a particularly interesting embodiment, drospirenone is delivered in a discontinuous manner such as delivery every third day, such as a 1-day-on-2-days-off regimen. This may be achieved by a regimen comprising administering a dosage unit comprising an estrogen sulphamate and drospirenone every third day and administering a dosage unit comprising an estrogen sulphamate but essentially absent in drospirenone on the other days of the regimen. Alternatively, an estrogen sulphamate may be delivered throughout the interval of the three days.

In a typical embodiment of the invention, the estrogen sulphamate is delivered in a continuous manner that may be effected by administration of a dosage unit at regular intervals e.g. 1 day, 3 days, 6 days, 7 days, 14 days, 28 days, 1 month, 3 months, 6 months, 9 months or 12 months. In a preferred embodiment, the estrogen sulphamate is delivered in a continuous manner comprising intervals of administration of 1 to 30 days, preferably 1, 3, 7, 14, 28 or 30 days, most preferably 1, 7, 28 or 30 days. In a presently preferred embodiment, the estrogen sulphamate is administered every 7 days.

In another typical embodiment of the invention, the estrogen sulphamate is delivered in a sequential manner, such as wherein the estrogen sulphamate is delivered for 18–30 followed by an interruption of delivery or 5–13 days; delivered for 19–28 days followed by an interruption of delivery of 6–12 days; or delivered for 21 days followed by an interruption of delivery of 7–10 days.

A particularly embodiment or the invention include the use of the combination of an estrogen sulphamate and drospirenone by administering both agents by means of oral administration. Further interesting aspects thereof includes the oral administration of drospirenone combined with transdermal, transvaginal or parenteral administration of an estrogen sulphamate. Combinations of transdermal administration and parenteral administration is also of interest.

The regimen may involve either the concomitant administration of an estrogen sulphamate and drospirenone or the independent administration of an estrogen sulphamate and drospirenone in a continuous or discontinuous manner.

An interesting embodiment of the regimen involve the delivery of an estrogen sulphamate in a continuous manner and drospirenone in a discontinuous manner, such regimen consisting of administering a dosage unit daily such that an estrogen sulphamate is delivered daily and drospirenone is delivered every second, third, or fourth, fifth, sixth or seventh day, preferably every third day. This may be accomplished by weekly administering a dosage unit comprising an estrogen sulphamate for a delivery of estrogen throughout that weekly interval and administering a dosage unit comprising drospirenone weekly, daily, or every 2, 3, 4, 5, or 6 days.

Hormone replacement therapy may be required for the remainder of the life of the woman experiencing deficient levels of estrogen the treatment involves administration of a combination of estrogen sulphamate and drospirenone over the course of a cycle according to an array of regimens depending on the needs of the woman. A regimen is typically related to a cycle regardless of whether a natural cycle actually exists in the woman. The method of treatment of the diseases, disorders or symptoms associated with deficient endogenous levels of estrogen in a woman involves administering the combination typically for a multiple of cycles, such as administering the combination for 1 to 12 cycles, preferably 2 to 6, such as 2, 3, 4, 5, and 6 multiples of 28 to 35 days. This may involve the administration of daily dosage units for each day of the 1 to 12 cycles.

A further aspect or the present invention relates to a kit for providing the sufficient dosages of the combination throughout the cycle the kit may comprise an oral formulation of one or both agents. The kit may comprise an oral formulation of one agent and a topical, transdermal, subcutaneous, transvaginal or parenteral formulation of the other agent. Typically, the kit comprises an oral formulation of both agents. The oral formulations may be such that one agent is delivered in a continuous manner and the other agent is delivered in a discontinuous manner.

The kit is typically designed to increase patient-compliance to follow the regimen.

Thus, an interesting aspect of the invention relates to a pharmaceutical kit comprising up to 70 dosage units or multiples thereof, wherein at least 3 said dosage units within one multiple of units comprise an estrogen sulphamate and at least 3 said dosage units within one multiple of units comprise drospirenone; and wherein optionally up to 64 of said dosage units within one multiple of units comprise a placebo or a blank.

The term "multiples thereof" is denoted to mean replicates of a set of dosage units. For example a set or 70 dosage units may be replicated into 140, 210, 280 and 350 dosage units. Preferably, a set of dosage units is replicated 2 to 12 times.

In suitable embodiments thereof, the estrogen sulphamate and drospirenone is combined in one dosage unit. Alternatively, the estrogen sulphamate and drospirenone is in separate dosage units. That is to say that the kit may comprise dosage units only comprising one if the active agents such as the estrogen sulphamate or the drospirenone. However, in some embodiments the dosage units comprise both the estrogen sulphamate and the drospirenone.

In the embodiment where the dosage units comprises both the estrogen sulphamate and the drospirenone, the pharmaceutical kit may comprise up to 35 dosage units or multiples thereof, wherein at least 3 said dosage units within one multiple of units comprise a combination of an estrogen sulphamate and drospirenone; and wherein optionally up to 32 of said dosage units within one multiple of units comprise a placebo or a blank. Such a kit may further comprise at least one estrogen sulphamate-free dosage unit within one multiple of units, said dosage unit comprising drospirenone. In suitable embodiments, the pharmaceutical kit comprises 4 to 12, preferably 4 to 10, most preferably 4 dosage units within one multiple of units comprising a combination of an estrogen sulphamate and drospirenone In suitable embodiments of the invention, the pharmaceutical kit comprises dosage units comprising the combination of an estrogen sulphamate and drospirenone as well as estrogen sulphamate-free dosage units comprising drospirenone. Thus, in other embodiments of the invention, the pharmaceutical kit comprises 4 to 10 dosage units within one multiple of units comprising a combination of an estrogen sulphamate and drospirenone and from about 10 to 24, such as 10, 11, 12, 15, 16, 17, 18, 19, 20, 21 or 24 sulphamate-free dosage unit comprising drospirenone In a suitable embodiment of the invention the pharmaceutical kit comprises at least 21 said dosage units comprising a combination of an estrogen sulphamate and drospirenone. This kit may further comprise at least 7 estrogen sulphamate-free dosage units comprising drospirenone.

In an alternative embodiment, the pharmaceutical kit further comprises no more than 7 said dosage units within one multiple of units comprising a placebo or a blank. That is to say that these no more than 7 dosage units are substantially free of an estrogen sulphamate and drospirenone.

As mentioned, the pharmaceutical kit of the invention may comprise the estrogen sulphamate and the drospirenone in separate dosage units such a kit comprises up to 70 dosage units within one multiple of dosage units, wherein at least 3 of those comprises an estrogen sulphamate and another at least three dosage units comprise drospirenone. Such a kit may further comprise at least one dosage unit comprising drospirenone. In another embodiment, such a kit may comprise at least 21 said dosage units comprising an estrogen sulphamate and at least 21 said dosage units comprising drospirenone. This kit may further comprise at least 7 said dosage units comprising drospirenone and still further comprise no more than 7 dosage units comprising a placebo or a blank. In suitable embodiments of the invention, the kit comprises 4 to 12, such as 4 to 10, preferably 4 dosage units comprising an estrogen sulphamate and 4 to 12, such as 4 to 10, preferably 4 estrogen-sulphamate-free dosage units comprising drospirenone. In other embodiments, the kit comprises 4 to 12, such as 4 to 10, preferably 4 dosage units comprising an estrogen sulphamate and 10 to 30, such as 15 to 30, such as 20 to 28 sulphamate-free dosage unit dosage units comprising drospirenone The pharmaceutical kit typically comprises of daily dosage units separately packaged as individually removable daily dosage units in a packaging unit and intended for oral administration for a period of at least 28 to 31 consecutive days. The dosage units comprising an estrogen sulphamate and/or drospirenone may comprise varying amounts of said estrogen sulphamate and/or drospirenone. The administration may alternatively be such that the said dosage units are administered once per three days, once per week, once per two week, once per four weeks or once per month. Furthermore some dosage units within a packaging unit may be for daily administration and other dosage units for weekly administration. Alternatively to oral administration, the dosage units may be for transdermal or subcutaneous administration.

According to the invention, the estrogen sulphamate-containing dosage units of the kit comprise estrogen sulphamate in a dose corresponding to about 0.01 to 25 mg of the unsubstituted 17-estradiol-sulphamate, preferably of about 0.05 to 6 mg, more preferably of about 0.1 to 4 mg, even more preferably of about 0.1 to 3 mg, most preferably of about 0.2 to 2 mg. Moreover, the drospirenone-containing dosage units comprise said drospirenone in a dose of about 0.1 to 10 mg, preferably of about 0.25 to 6 mg, more preferably of about 0.25 to 4 mg, even more preferably of about 0.25 to 3 mg, most preferably or about 0.25 to 4 mg.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The entire disclosure[s] of all applications, patents and publications, cited above or below, and of corresponding Denmark Application No. PA200101109, filed Jul. 13, 2001, and U.S. Provisional Application Ser. No. 60/304,760, filed Jul. 13, 2001, are hereby incorporated by reference.

EXAMPLES

Example 1

Prevention of Bone Demineralisation

Primary Objective: Bone mineral density after 2 years of treatment.

Secondary Objectives. Bone mineral density of the hip after 12, 28, 52, and 80 weeks of treatment. Bone mineral density of the lumbar spine.

The study will be conducted as a double blind, placebo-controlled trial with 100 healthy, post-menopausal women randomly assigned to one of 2 groups of 50 (active or placebo) after giving their informed consent.

| Active group | 750 µg of estradiol sulphamate + 3 mg drospirenone |
|---|---|
| Placebo group: | placebo tablet |

Synopsis

Fifty 20 non-osteopenic patients should be enrolled in each group. All treatments will be applied once per week per os during the whole treatment of 2 years without a treatment-free interval. In addition, the patients will be supplied with calcium tablets (500 mg of calcium daily). Measurements of bone mineral density of the hip will be measured on the left side utilising dual-energy x-ray absorptiometry at screening, baseline, and after 12, 28, 52, 80, and 104 weeks of treatment. Biochemical markers of bone remodelling will be measured at intervals.

Evaluation:

The increase of bone mineral density is measured to establish that the density is statistically larger that that observed in the placebo group.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

I claim:

1. A dosage unit in a form for oral administration comprising a combination of:
   i) an estrogen sulphamate; and
   ii) drospirenone;
   together with one or more pharmaceutically acceptable carriers or excipients, wherein the estrogen sulphamate is in an amount effective for at least a period of 3 days.

2. The dosage unit according to claim 1, wherein the estrogen sulphamate is selected from the group consisting of unsubstituted 17-estradiol-sulphamate, unsubstituted 16,17-estriol-sulphamate, 17-estradiol-3-N,N-dimethyl sulphamate and 16,17-estriol-3-N,N-dimethyl sulphamate.

3. The dosage unit according to claim 1, wherein the estrogen sulphamate is unsubstituted 17-estradiol-sulphamate and it is present in an amount of about 0.03 to 3 mg.

4. The dosage unit according to claim 1, wherein the estrogen sulphamate is unsubstituted 17-estradiol-sulphamate and it is present in an amount of about 0.2 to 1.5 mg.

5. The dosage unit according to claim 1, wherein the estrogen sulphamate is unsubstituted 17-estradiol-sulphamate in an amount of about 0.1 to 6 mg effective for about one week.

6. The dosage unit according to claim 1, wherein the estrogen sulphamate is unsubstituted 17-estradiol-sulphamate in an amount of about 0.4 to 25 mg.

7. The dosage unit according to claim 1, wherein the drospirenone is in a dose effective for at least a period of 3 days.

8. The dosage unit according to claim 7, wherein the drospirenone is in an amount of about 0.25 mg to 15 mg.

9. The dosage unit according to claim 3, wherein the drospirenone is in an amount of about 0.25 mg to 15 mg.

10. The dosage unit according to claim 1, wherein drospirenone is in a dose corresponding to a weekly delivery of about 1 mg to 20 mg.

11. The dosage unit according to claim 1, wherein drospirenone is in a dose of about 2 to 75 mg.

12. The dosage unit according to claim 1, formulated for slow release of drospirenone.

13. The dosage unit according to claim 1, formulated for normal release of drospirenone.

14. The dosage unit according to claim 1, formulated for slow release of the estrogen sulphamate.

15. The dosage unit according to claim 1, formulated for normal release of the estrogen sulphamate.

16. The dosage unit according to claim 1, wherein the dose of the estrogen sulphamate is sufficient for the treatment of diseases, disorders or symptoms associated with deficient endogenous levels of estrogen in a woman throughout a period selected from 3 days, 7 days, 14 days, 28 days and 1 month after administration of one of said dosage unit.

17. The dosage unit according to claim 1, wherein the dose of drospirenone is in an amount effective for a period selected from 1 day, 3 days, 7 days, 14 days, 28 days and 1 month after administration of one of said dosage unit.

18. The dosage unit according to claim 1, in a form of a tablet, a capsule, a granule or a powder.

19. A method of treating a disease, disorder or symptom associated with deficient endogenous levels of estrogen in a woman comprising: administering a sufficient dose of estrogen sulphamate to alleviate said disease, disorder or symptom in combination with drospirenone, wherein the estrogen sulphamate is administered orally either: every third day; once a week; for three days followed by three days of no administration; or for seven days followed by seven days of no administration.

20. The method according to claim 19, wherein the deficient endogenous levels of estrogen are caused by natural menopause, pre-menopause, peri-menopause, post-menopause, hypogonadism, castration, hysterectomy, and/or primary ovarian failure.

21. The method according to claim 19, wherein the disease, disorder or symptom is selected from the group consisting of: hot flushes, sweating attacks, palpitations, sleep disorders, mood changes, nervousness, anxiety, poor memory, loss of confidence, loss of libido, poor concentration, diminished energy, diminished drive, irritability, urogenital atrophy, atrophy of the breasts, cardiovascular disease, changes in hair distribution, thickness of hair, changes in skin condition, breast cancer, bone demineralisation and osteoporosis.

22. The method according to claim 19, wherein the disease, disorder or symptom is selected from the group consisting of: sleep disorders, mood changes, nervousness, anxiety, urogenital atrophy, atrophy of the breasts, breast cancer, bone demineralization and osteoporosis.

23. The method according to claim 19, wherein the dose of estrogen sulphamate is sufficient for the prevention of bone demineralisation in a woman or for the management of osteoporosis.

24. The method according claim 19, wherein the dose of estrogen sulphamate is sufficient for the treatment of breast cancer in a woman.

25. The method according to claim 19, wherein the estrogen sulphamate is selected from the group consisting of: unsubstituted 17-estradiol-sulphamate, unsubstituted 16,17-estriol-sulphamate, 17-estradiol-3-N,N-dimethyl sulphamate and 16,17-estriol-3-N,N-dimethyl sulphamate.

26. The method according to claim 19, wherein the estrogen sulphamate is unsubstituted 17-estradiol-sulphamate and the dose is an amount of about 0.03 to 3 mg.

27. The method according to claim 19, wherein the estrogen sulphamate is unsubstituted 17-estradiol-sulphamate and the dose is an amount of about 0.1 to 2.5 mg.

28. The method according to claim 19, wherein the estrogen sulphamate is unsubstituted 17-estradiol-sulphamate and the dose is an amount of about 0.1 to 6 mg which is effective for about one week.

29. The method according to claim 19, wherein the estrogen sulphamate is unsubstituted 17-estradiol-sulphamate and the dose is an amount of about 0.4 to 25 mg.

30. The method according to claim 19, wherein drospirenone is in a sufficient dose to exhibit its anti-androgenic and/or anti-mineralcorticoid activity in a woman.

31. The method according to claim 30, wherein the dose of drospirenone is about 0.25 mg to 15 mg.

32. The method according to claim 30, wherein the dose of drospirenone is about 1 mg to 5 mg.

33. The method according to claim 30, wherein the dose of drospirenone is about 1 mg to 20 mg and is effective in exhibiting its anti-androgenic and/or anti-mineralcorticoid activity for about one week.

34. The method according to claim 30, wherein the dose of drospirenone is about 2 to 75 mg.

35. The method according to claim 30, wherein the combination is administered in a single dosage unit or as more than one dosage unit.

36. The method according to claim 35, wherein estrogen sulphamate and drospirenone are concomitantly administered.

37. The method according to claim 35, wherein estrogen sulphamate and drospirenone are independently administered.

38. The method according to claim 35, wherein estrogen sulphamate and drospirenone are administered in a continuous manner.

39. The method according to claim 35, wherein estrogen sulphamate and drospirenone are administered in a discontinuous manner.

40. The method according to claim 35, wherein the estrogen sulphamate is delivered in a continuous manner and drospirenone in a discontinuous manner.

41. The method according to claim 40, wherein the estrogen sulphamate is delivered for 18–30 days followed by an interruption of delivery of 5–13 days;

delivered for 19–28 days followed by an interruption of delivery of 6–12 days; or delivered for 21 days followed by an interruption of delivery of 7–10 days.

42. The method according to claim 38, wherein the continuous manner comprises intervals of administration of 3, 7, 14, or 30 days.

43. The method according to claim 40, wherein drospirenone is administered in a discontinuous manner of:

1 day followed by an interruption for 1 to 30 days;

2 days followed by an interruption for 1 to 29 days;

3 days followed by an interruption for 1 to 28 days;

4 days followed by an interruption for 1 to 27 days;

5 days followed by an interruption for 1 to 26 days;

6 days followed by an interruption for 1 to 25 days;

7 days followed by an interruption for 1 to 24 days;

10 days followed by an interruption for 1 to 21 days;

14 days followed by an interruption for 1 to 17 days;

17 days followed by an interruption for 1 to 14 days; or 21 days followed by an interruption for 7 to 10 days;

or combinations thereof.

44. The method according to claim 19, wherein the estrogen sulphamate is administered weekly and drospirenone is administered daily.

45. The method according to claim 19, wherein the combination of the estrogen sulphamate and drospirenone is administered weekly.

46. The method according to claim 19, wherein the drospirenone is administered in the form of an oral, topical, transdermal, subcutaneous, transvaginal or parenteral formulation, or a mixture thereof.

47. The method according to claim 19, wherein the combination of the estrogen sulphamate and drospirenone is administered for 1 to 12 multiples of 28 to 35 days.

48. The method according to claim 19, wherein the combination of the estrogen sulphamate and drospirenone is administered weekly for 1 to 6 multiples of 4 to 12 weeks.

49. The method according to claim 30, wherein the anti-androgenic and/or anti-mineralcorticoid activity of the drospirenone results in prevention or counteraction of at least one of the following adverse effects of the estrogen sulphamate: adverse effects to the endometrium; prevention or lessening of weight gain; and prevention or lessening of changes in hair pattern, texture, growth or distribution.

50. A pharmaceutical kit comprising up to 70 dosage units or multiples thereof, wherein at least 3 of said dosage units within one multiple of units comprise an estrogen sulphamate and at least 3 of said dosage units within one multiple of units comprise drospirenone; and wherein optionally up to 64 of said dosage units within one multiple of units comprise a placebo or a blank, wherein the dosage units are formulated for being administered orally in intervals selected from once per three days, once per week, once per two week, once per four weeks, once per month and combinations thereof.

51. The pharmaceutical kit according to claim 50, wherein at least one dosage unit comprises a combination of the estrogen sulphamate and drospirenone.

52. The pharmaceutical kit according to claim 50, wherein the estrogen sulphamate and drospirenone are in separate dosage units.

53. The pharmaceutical kit according to claim 51 comprising up to 35 dosage units or multiples thereof, wherein at least 3 of said dosage units within one multiple of units comprise a combination of an estrogen sulphamate and drospirenone; and wherein optionally up to 32 of said dosage units within one multiple of units comprise a placebo or a blank.

54. The pharmaceutical kit according to claim 53, further comprising at least one estrogen sulphamate-free dosage unit within one multiple of units, said dosage unit comprising drospirenone.

55. The pharmaceutical kit according to claim 53, wherein at least 21 dosage units within one multiple of units comprise a combination of the estrogen sulphamate and drospirenone.

56. The pharmaceutical kit according to claim 55, further comprising at least 7 estrogen sulphamate-free dosage units within one multiple of units, said dosage units comprising drospirenone.

57. The pharmaceutical kit according to claim 55, further comprising no more than 7 dosage units within one multiple of units comprising a placebo or a blank.

58. The pharmaceutical kit according to claim 52, wherein within one multiple of units at least 21 said dosage units comprise estrogen sulphamate and at least 21 said dosage units comprise drospirenone.

59. The pharmaceutical kit according to claim 58, comprising no more than 7 dosage units within one multiple of units comprising a placebo or a blank.

60. The pharmaceutical kit according to claim 52, wherein within each multiple of units at least 3 dosage units comprise the estrogen sulphamate and at least 21 dosage units comprise drospirenone.

61. The pharmaceutical kit according to claim 50, wherein the estrogen sulphamate is selected from the group consisting of the unsubstituted 17-estradiol-sulphamate, unsubstituted 16,17-estriol-sulphamate, 17-estradiol-3-N,N-dimethyl sulphamate and 16,17-estriol-3-N,N-dimethyl sulphamate.

62. The pharmaceutical kit according to claim 50, wherein the estrogen sulphamate is the unsubstituted 17-estradiol-sulphamate.

63. The pharmaceutical kit according to claim 50, wherein said estrogen sulphamate-containing dosage units comprise unsubstituted 17-estradiol-sulphamate in a dose of about 0.01 to 25 mg.

64. The pharmaceutical kit according to claim 50, wherein said drospirenone-containing dosage units comprise said drospirenone in a dose of about 0.1 to 10 mg.

65. The pharmaceutical kit according to claim 50, comprising dosage units with different doses of said estrogen sulphamate.

66. The pharmaceutical kit according to claim 50, comprising dosage units with different doses of said drospirenone.

67. The dosage unit according to claim 1, wherein the estrogen sulphamate is in an amount which remains effective for a period of 7 days after administration of one said dosage unit.

68. The dosage unit according to claim 1, wherein the estrogen sulphamate is in an amount which remains effective for a period of 14 days after administration of one said dosage unit.

69. The dosage unit according to claim 1, wherein the estrogen sulphamate is in an amount which remains effective for a period of 28 days after administration of one said dosage unit.

70. The dosage unit according to claim 1, wherein the estrogen sulphamate is in an amount which remains effective for a period of 1 month after administration of one said dosage unit.

71. The dosage unit according to claim 1, wherein the estrogen sulphamate is unsubstituted 17-estradiol-sulphamate.

* * * * *

UNITED STATES PATENT AND TRADEMARK OFFICE
CERTIFICATE OF CORRECTION

PATENT NO. : 6,869,941 B2  Page 1 of 1
APPLICATION NO. : 10/194970
DATED : March 22, 2005
INVENTOR(S) : Rolf Schuermann et al.

It is certified that error appears in the above-identified patent and that said Letters Patent is hereby corrected as shown below:

On the front page, (75) Inventors: insert second Inventor -- Walter elger, Berlin (DE) --

Signed and Sealed this

Eighth Day of August, 2006

JON W. DUDAS
*Director of the United States Patent and Trademark Office*

UNITED STATES PATENT AND TRADEMARK OFFICE
CERTIFICATE OF CORRECTION

PATENT NO. : 6,869,941 B2  
APPLICATION NO. : 10/194970  
DATED : March 22, 2005  
INVENTOR(S) : Rolf Schuermann et al.

Page 1 of 1

It is certified that error appears in the above-identified patent and that said Letters Patent is hereby corrected as shown below:

On the front page, (75) Inventors: insert second Inventor -- Walter Elger, Berlin (DE) --

Signed and Sealed this

Twelfth Day of September, 2006

JON W. DUDAS  
*Director of the United States Patent and Trademark Office*